(12) United States Patent
Kusters et al.

(10) Patent No.: US 9,533,135 B2
(45) Date of Patent: Jan. 3, 2017

(54) METHOD FOR FORMING, OPENING AND/OR EVALUATING A CONNECTION SITE

(71) Applicant: Fenwal, Inc., Lake Zurich, IL (US)

(72) Inventors: Benjamin E. Kusters, Pleasant Prarie, WI (US); Kyungyoon Min, Kildeer, IL (US)

(73) Assignee: Fenwal, Inc., Lake Zurich, IL (US)

( * ) Notice: Subject to any disclaimer, the term of this patent is extended or adjusted under 35 U.S.C. 154(b) by 100 days.

(21) Appl. No.: 14/309,327

(22) Filed: Jun. 19, 2014

(65) Prior Publication Data
US 2015/0367120 A1    Dec. 24, 2015

(51) Int. Cl.
| | |
|---|---|
| *A61M 39/10* | (2006.01) |
| *A61M 39/14* | (2006.01) |
| *B26F 1/26* | (2006.01) |
| *B26F 3/00* | (2006.01) |
| *F16L 13/00* | (2006.01) |
| *A61M 39/08* | (2006.01) |
| *A61M 39/18* | (2006.01) |

(52) U.S. Cl.
CPC .......... *A61M 39/146* (2013.01); *A61M 39/08* (2013.01); *A61M 39/18* (2013.01); *B26F 1/26* (2013.01); *B26F 3/00* (2013.01); *F16L 13/00* (2013.01); *A61M 2039/087* (2013.01); *A61M 2205/15* (2013.01); *A61M 2205/70* (2013.01); *A61M 2207/00* (2013.01); *Y10T 137/0447* (2015.04); *Y10T 137/1714* (2015.04)

(58) Field of Classification Search
CPC .............. B26F 1/26; B26F 3/00; A61M 39/10
USPC ................................ 137/68.11, 68.17, 68.23
See application file for complete search history.

(56) References Cited

U.S. PATENT DOCUMENTS

| | | | | |
|---|---|---|---|---|
| 3,300,283 | A * | 1/1967 | Lauer ......................... | B01J 3/08 137/68.23 |
| 4,439,188 | A | 3/1984 | Dennehey et al. | |
| 4,596,551 | A | 6/1986 | Golinski et al. | |
| 6,565,526 | B2 * | 5/2003 | Seward ................. | A61M 39/24 137/859 |
| 2003/0089446 | A1 | 5/2003 | Baradon et al. | |
| 2008/0051708 | A1 * | 2/2008 | Kumar ................ | A61M 1/0031 604/119 |

(Continued)

FOREIGN PATENT DOCUMENTS

| | | |
|---|---|---|
| EP | 0134630 B | 5/1989 |
| EP | 0507321 B1 | 6/1995 |

(Continued)

OTHER PUBLICATIONS

Brueckner Thomas, Feb. 2012, WO 2012022635 A2, DE.*
Extended European Search Report dated Oct. 28, 2015 for EP Application No. 15171553.9-1702.

*Primary Examiner* — John K Fristoe, Jr.
*Assistant Examiner* — Paul Gray
(74) *Attorney, Agent, or Firm* — Cook Alex Ltd.

(57) ABSTRACT

System, apparatus and method for opening a heat-bonded connection formed between two hollow, flexible thermoplastic conduits. A pressure difference is created between the inside of at least one of the conduits and the ambient atmosphere sufficient to cause expansion of a wall of the tubing conduit in the vicinity of a frangible portion at least partially blocking the connection to disrupt the frangible portion and reduce the blocking.

19 Claims, 6 Drawing Sheets

(56) References Cited

U.S. PATENT DOCUMENTS

| | | |
|---|---|---|
| 2009/0302033 A1 | 12/2009 | Barr |
| 2013/0153048 A1 | 6/2013 | Schwalm et al. |
| 2015/0367569 A1 | 12/2015 | Kusters |

FOREIGN PATENT DOCUMENTS

| | | |
|---|---|---|
| EP | 0723851 A2 | 7/1996 |
| EP | 0471953 B1 | 9/1999 |
| EP | 0847847 B1 | 10/1999 |
| EP | 1048316 B1 | 1/2003 |
| EP | 1048315 B1 | 6/2005 |
| EP | 1579983 B1 | 4/2009 |
| EP | 1640142 B1 | 4/2011 |
| EP | 1740366 B1 | 11/2011 |
| EP | 2419257 B1 | 3/2013 |
| EP | 2046560 B1 | 5/2014 |
| EP | 1555111 B1 | 1/2015 |
| EP | 2957402 A1 | 12/2015 |
| WO | WO 2004/071690 A1 | 8/2004 |
| WO | WO 2013/048336 A1 | 4/2013 |
| WO | WO 2014/128972 A1 | 8/2014 |
| WO | WO 2015/060774 A1 | 4/2015 |

\* cited by examiner

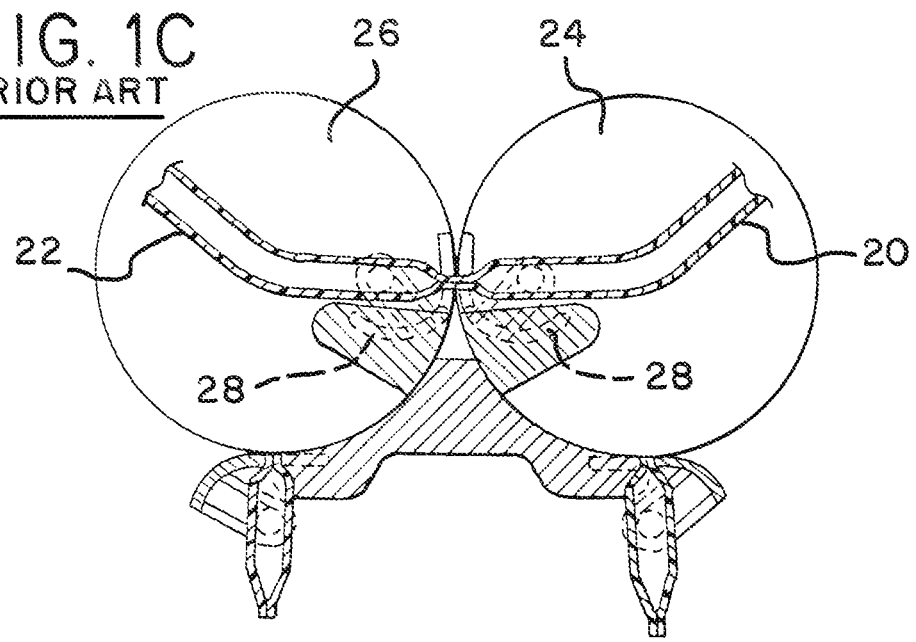

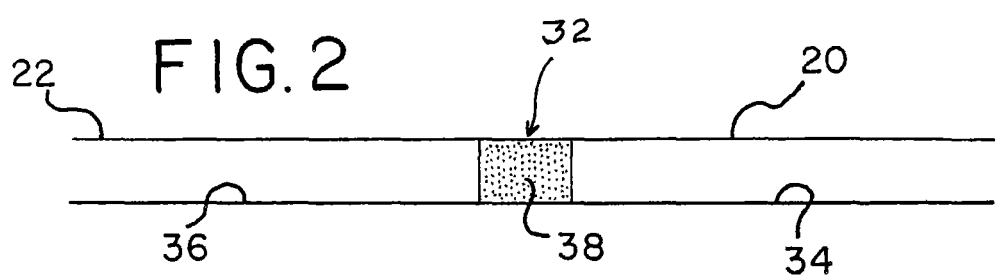
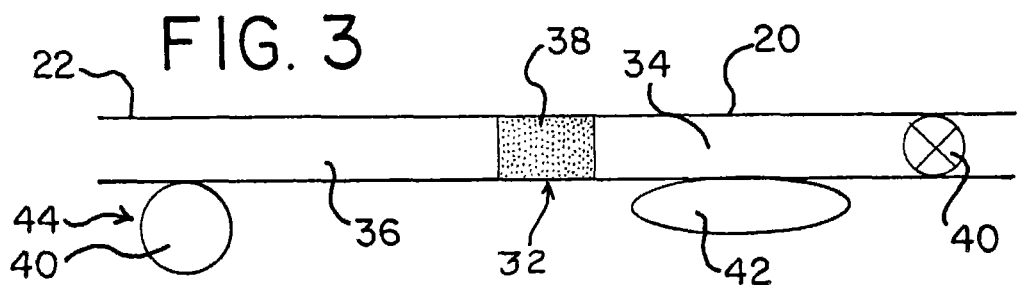
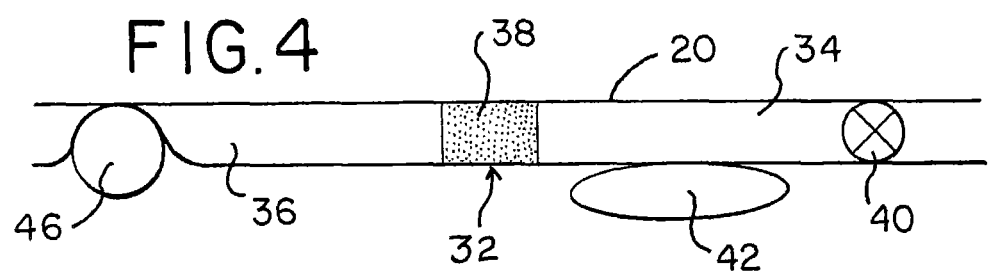
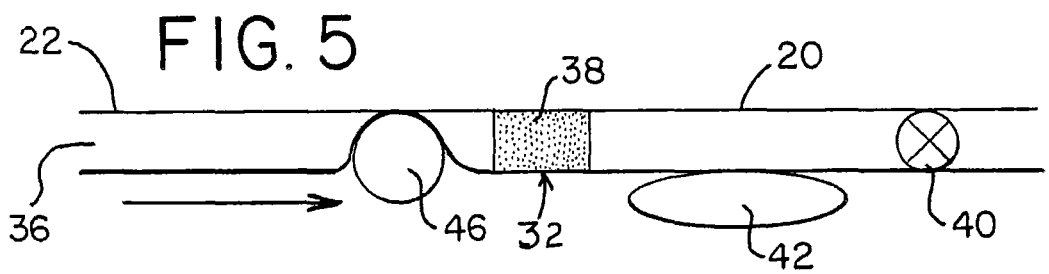
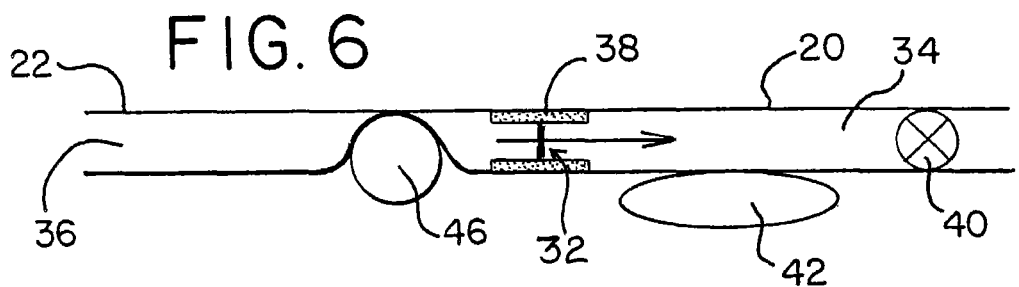

FIG. 10A
FIG. 10B
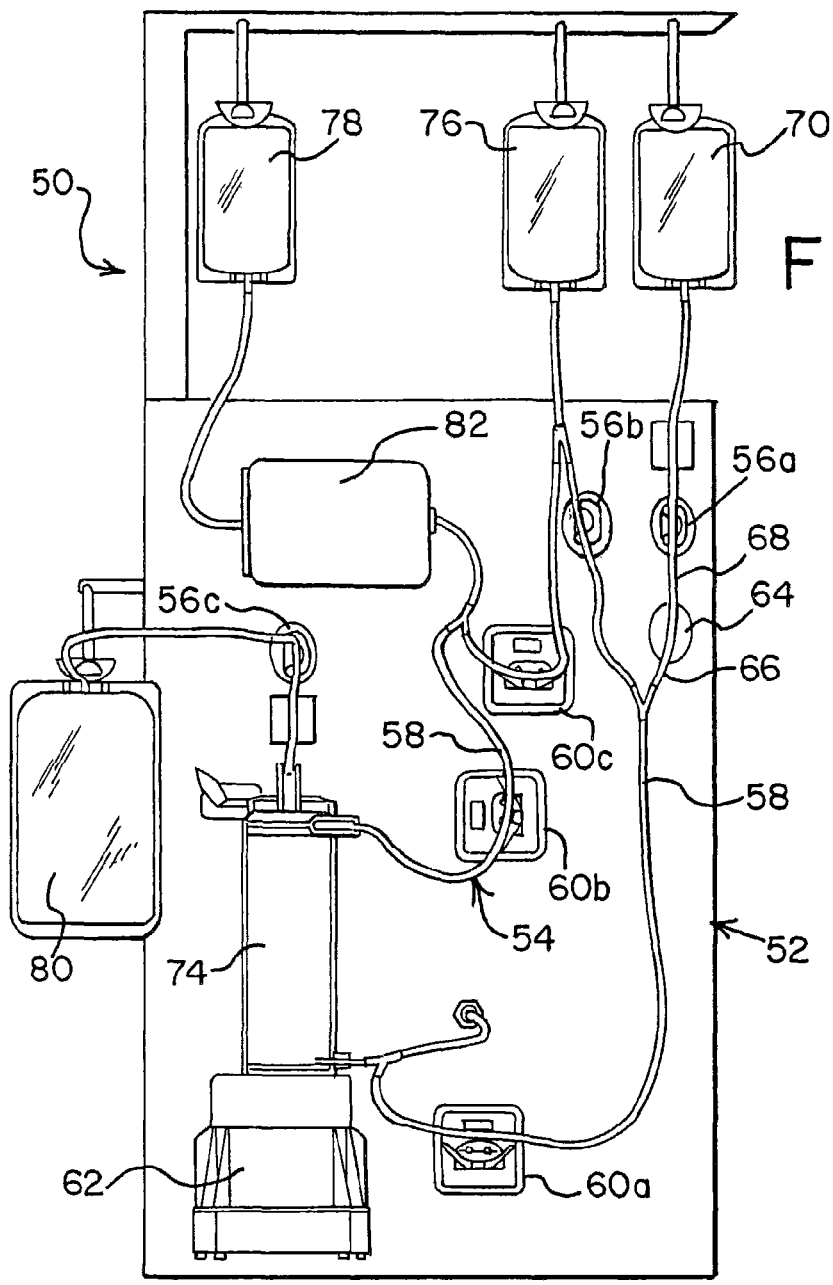
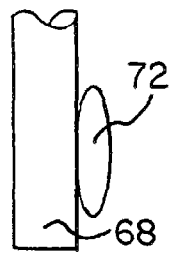
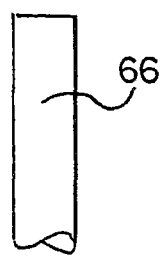

METHOD FOR FORMING, OPENING AND/OR EVALUATING A CONNECTION SITE

The present disclosure generally relates to apparatus and methods for opening and/or testing or evaluating a connection between two flexible thermoplastic conduits, such as, for example, fluid flow tubing in a medical fluid flow circuit employed in collecting, processing or treating blood or blood components.

It is well known in the medical industry in general and particularly in the blood banking field to use connection systems for connecting two separate tubing segments of a fluid flow set or circuit in a manner that prevents the introduction of contaminants or preserves the sterility of the tubing, if pre-sterilized, during the connection process. Such systems have found application both in the large scale assembly or manufacture of fluid flow circuits and in the hands of the ultimate user for on-site assembly of fluid flow circuits having a desired configuration. For example, a user may desire to carry out a particular medical procedure, such as for collecting, processing or treating blood and blood components. These devices or systems are commonly referred to in the medical field as sterile connection or sterile docking devices.

Known connection devices or systems include electron beam systems, as in U.S. Pat. No. 5,009,645; radiant energy systems that melt facing membranes of fluid flow conduits, as in U.S. Pat. No. 4,157,723 and heated wafer systems that employ wafers for cutting and heat bonding or splicing tubing segments together while the ends remain at a molten or semi-molten elevated temperature, such as in U.S. Pat. Nos. 4,753,697, 5,158,630 and 5,156,701.

More recently, a novel connection system and apparatus has been described that connects flexible thermoplastic tubing segments by heat or melt bonding the ends together while the ends are individually clamped into a closed position, preventing ambient contamination. Such a system is described in detail in U.S. published patent application no. 2013/0153048, which is incorporated by reference herein in its entirety. The connection made by such apparatus has a temporary closed condition or crimped shape due to the high temperature and clamping of the ends during connection. At the connection site, as a result of the connection process, a portion of thermoplastic material such as a "skin", "membrane" or "web" from the tubing, closes or reduces the cross section of the tubular portions or segments. This thermoplastic blocking portion of the connection can be broken or otherwise disrupted to open it by light (in particular manual) external pressure or manipulation onto the connection point or site.

The present apparatus and methods have particular application with respect to the novel connection system described in the preceding paragraph. More particularly, the subject matter of this description provides a means and method to break or otherwise disrupt the thermoplastic portion and therefore more fully open such a connection site to allow or improve fluid flow between the conduits, without requiring external manipulation. Optionally, the present apparatus and method also provides means and method for testing or evaluating the integrity of a connection site after opening, although this aspect may also be used by itself, without the opening aspect, for testing such connections made using the above or other connection techniques.

Turning now to a more detailed description of the present subject matter, which is presented for purposes of description and not limitation, various aspects and features of the present subject are seen in the attached drawings, of which:

FIGS. 1a-1c show, for background purposes, the device and method for forming a heat-bonded connection described in U.S. published patent application no. 2013/0153048, which is herein incorporated by reference in its entirety.

FIG. 2 is a diagrammatic sectional view of two flexible, hollow, thermoplastic conduits or tubing segments joined by a connection (illustrated by the darkened area) of the type resulting from the apparatus and method described in U.S. Pub. No. 2013\0153048.

FIG. 3 is a diagrammatic sectional view of two flexible, hollow, thermoplastic conduits or tubing segments as in FIG. 2, in combination with apparatus of the present disclosure, showing one conduit occluded on one side of the connection site, a pressure or force sensor between the occlusion and the connection site and roller or peristaltic type pump in contact with the other conduit (on the other side of the connection site).

FIG. 4 is a diagrammatic sectional view like FIG. 2 and illustrating the pump engaging and occluding the other conduit.

FIG. 5 is a diagrammatic sectional view like FIG. 2 and illustrating movement of the pump roller toward the connection site to increase internal pressure in the other conduit.

FIG. 6 is a diagrammatic sectional view like FIG. 2 and illustrating the increase in pressure in the other conduit causing disruption of the connection site to open it for fluid flow between the conduits.

FIG. 10a is an elevational view depicting how the present subject matter may be employed on particular apparatus for processing blood, blood components or other biological or other fluids.

FIG. 10b is an enlarged diagrammatic view of a portion of the apparatus of FIG. 10a showing apparatus of the present disclosure for opening and/or checking the integrity of a heat-bonded connection in a disposable fluid circuit employed with the apparatus.

Figure 15A:
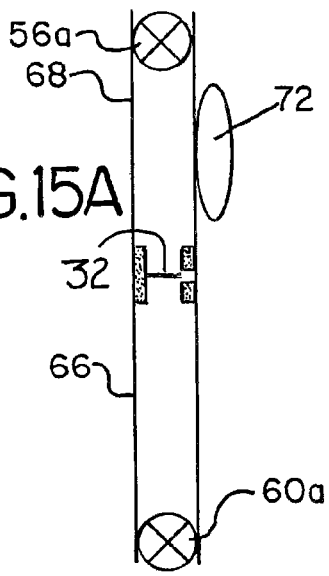
Figure 15B:
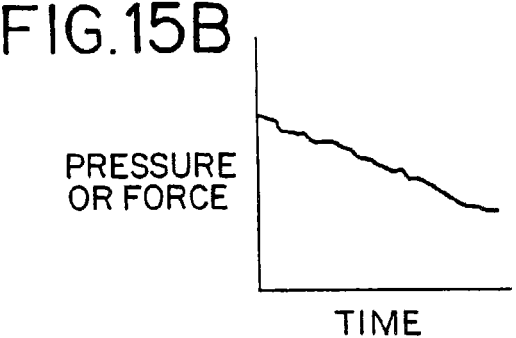

FIGS. 15a and 15 b are diagrammatic views of the portion shown in FIG. 10b, illustrating integrity check of a connection site that is not intact and is experiencing external leakage and the typical pressure/force vs. time graph that would reflect such as connection site to the sensor.

SUMMARY OF DISCLOSURE

The following is to provide a summary of various embodiments and/or aspects of the present subject matter and is not intended to include every embodiment or aspect or to provide a more detailed description, which may be found in the later detailed description.

In accordance with one aspect of the present subject matter, a method is provided for opening a heat-bonded connection formed between two hollow, flexible, thermoplastic conduits, which connection includes a portion of thermoplastic material at least partially blocking internal communication between the conduits. In one embodiment the method includes creating a pressure difference between the inside of at least one of the conduits and the ambient atmosphere sufficient to cause expansion of the conduit in the vicinity of the thermoplastic portion to disrupt the frangible portion and reduce the blocking. By reducing the blocking, it is not meant that the effect of the blocking is completely removed, but that the amount of blockage is reduced so that improved flow (which may differ significantly in different applications) is provided through the connection site.

In accordance with another embodiment, the pressure difference or differential optionally may be created when the thermoplastic material at an elevated temperature, such as an elevated temperature that is the result of heating that occurs during a heat bonding process. The increased pressure difference may also be created when the connection site is at ambient temperature, but for a given connection site and conduit material and thickness, less pressure difference may be required if the thermoplastic material is at an elevated temperature.

If the pressure differential is created while the connection site is at an elevated temperature, in one embodiment the pressure difference is created when the thermoplastic material has a temperature where it is still relatively soft or at least not fully hardened, such as optionally above its glass transition temperature.

In accordance with another embodiment, the method of any of the above examples may be provided in which the pressure difference is created by increasing the pressure inside of the conduit above the ambient pressure.

In accordance with another embodiment, the method of any of above methods may be provided in which the pressure difference is created by reducing the pressure outside of the conduit below the pressure inside the conduit. This may be used alone or in combination with increasing the pressure within the conduit.

In another embodiment, any of the above methods may include occluding one or both of the thermoplastic conduits and increasing the pressure/force difference between the pressure inside the conduit(s) and the ambient environment until the frangible portion is disrupted. As explained above, this may be done by increasing the internal pressure in one of the conduits, decreasing the external pressure, or both.

Where the present subject matter is employed in combination with or sequentially to formation of a heat bond between the two conduits, such as that for example described in U.S. 2013/0153048, in accordance with another aspect, which may be used with any of the embodiments discussed above, the pressure difference may optionally be created, relatively soon after formation of the heat-bonded connection. For example, almost immediately after the connection is formed, the connection site can be opened with internal pressurization of one of the conduits to a pressure as low as about 200 mmHg (3.9 psi), but there is increased risk that opening this quickly will result in loss of connection integrity because the plastic is still too soft or molten. Preferably, but not exclusively, the pressure to open the connection site is applied after about 5 seconds to allow greater cooling of the connection site, but not more than about 10 seconds, as the pressure to open the connection site increases as the site cools. Allowing cooling for more than 10 seconds may require the use of excessive pressure to open the connection site At about 5-10 seconds after formation, the connection site can typically be opened by internal pressurization of one of the conduits to about 1000-1500 mmHg (19-29 psi). The pressures and times required may be varied with enhanced cooling or supplemental heating of the connection site In connection with a further aspect, any of the above embodiments may include observing the pressure/force difference in one or both of the conduits to detect disruption of the blocking portion at the connection site, and/or after the blocking portion is disrupted to determine the integrity of the heat-bonded connection site. In other words, the internal pressure or pressure differential could be observation from the about the time of disruption to detect whether the pressure/force difference remains relatively unchanged, reflecting that the connection site is intact, has integrity and is not leaking, or whether the pressure/force difference changes, i.e. reduces, suggesting the presence of a leak and lack of connection integrity. The observation for integrity could be done over a limited period of time. Large leaks would likely be detected relatively quickly, such as within about 5 seconds, by degradation of internal testing pressure. Detection of very small "pin hole" size leaks may require observation for as long as about 20-30 seconds. For safety purposes, the default observation time period or duration would be the longer time needed to better detect even small leakages, although that time period could be cut short if a large leak is detected earlier. The result could of course be reflected in an audible or visual signal, alarm or indication to a user so that, in the event of leakage, corrective action could be taken where feasible or the conduits and any associated fluid circuits could be discarded.

The above aspect, i.e., the testing of connection integrity by sensing pressure/force difference over a period of time, could also be used independently of any opening feature or benefit to evaluate the integrity of a heat bonded or other connection arrangement between two conduits in order to test for integrity of the connection site.

In a further aspect of any of the embodiments of the present subject matter employing observation of the pressure/force difference, the pressure difference could be increased until the monitoring detects disruption of the thermoplastic portion at the connection site. For example, where the pressure/force difference is increased by increasing pressure within a particular conduit, the pressure/force in the other connected conduit may be observed, and disruption and opening of the connection site evidenced by increase in pressure in the other connected conduit. It is understood that the pressure/force difference, regardless of how created, could have an upper limit, which is the burst pressure of the conduit. If disruption is not detected by the time the pressure/force difference nears the burst pressure or is within a selected safety margin, the pressure increase can be stopped and the user alerted that manual manipulation to open the connection site or other action may be required. As explained earlier, the disruption of the thermoplastic portion blocking the connection site may optionally be followed by monitoring of the pressure in the joined conduits such as for a period of time to evaluate connection integrity.

In another embodiment of the present subject matter, connection opening apparatus is provided for opening a heat-bonded connection formed between two hollow, flexible, thermoplastic conduits, which connection includes a portion of thermoplastic material at least partially blocking internal communication between the conduits. The apparatus comprises an occluder, such as but not limited to a valve or clamp, cooperative with one of the thermoplastic conduits to block flow through the conduit, a pump cooperative with the other of the other of the fluid conduits to create pressure within the other of the fluid conduits in proximity to such a connection and a pressure sensor cooperative with the one thermoplastic conduit and operable to sense pressure inside the one conduit. In this arrangement, pressure from the pump is operable to disrupt the blocking portion to reduce the amount of blocking and the sensor is operable to sense pressure in the one conduit, for example, to sense a pressure increase in the one conduit in response to disruption of the blocking portion.

In the apparatus of the above embodiment, the sensor may optionally be configured to sense pressure for a period of time after disruption of the blocking portion to assess connection integrity. As explained briefly earlier, the above apparatus also may be configured to provide only a check of the integrity of a heat bonded conduit connection that is formed by other types of apparatus or methods.

In connection with yet a further embodiment, a durable blood processing device is provided for processing blood in a disposable fluid circuit of the type including a blood separator and an associated fluid flow tubing circuit. The durable processing device may comprise a station for receiving a blood separator, at least one control valves for controlling flow through the fluid circuit, and apparatus for opening a heat-bonded connection in the fluid circuit, which connection is formed between two flexible, hollow, thermoplastic conduits, and includes a portion of thermoplastic material at least partially blocking internal communication between the conduits. The opening apparatus includes a valve cooperative with one of the conduits to block flow therethrough, a pump cooperative with the other of the conduits to create pressure within the other of the fluid conduits in proximity to such a connection to disrupt the blocking portion and thereby reduce the amount of blocking, and a pressure sensor cooperative with the one conduit and operable to sense pressure inside the one conduit.

In another embodiment, the above durable blood processing device further includes connection apparatus for forming a heat-bonded connection between two thermoplastic conduits of a disposable fluid flow circuit, which connection includes a portion of thermoplastic material at least partially blocking internal communication between the conduits. The connection forming apparatus may be located on the durable processing device so as to form such connection between the valve and sensor on one side of the connection and the pump on the other side of the connection.

In connection with another embodiment, a connection system is provided for forming a heat-bonded connection between two hollow, flexible, thermoplastic conduits. The system includes connection forming apparatus and connection opening apparatus. The connection forming apparatus includes at least two relatively pivotable or rotatable members, each cooperative with a separate thermoplastic conduit so as to pivotally or rotatably move ends of the respective conduits between a spaced-apart position and an end-to-end contacting position for forming a heat-bonded connection therebetween. The connection opening apparatus includes a valve cooperative with one of the conduits to block flow therethrough; a sensor cooperatively associated with the one of the conduits for sensing pressure inside of the one conduit between the connection and the valve, and a pump cooperative with the other of the conduits to increase pressure within the other of the conduits to disrupt and open the connection.

DETAILED DESCRIPTION

Figure 1A:
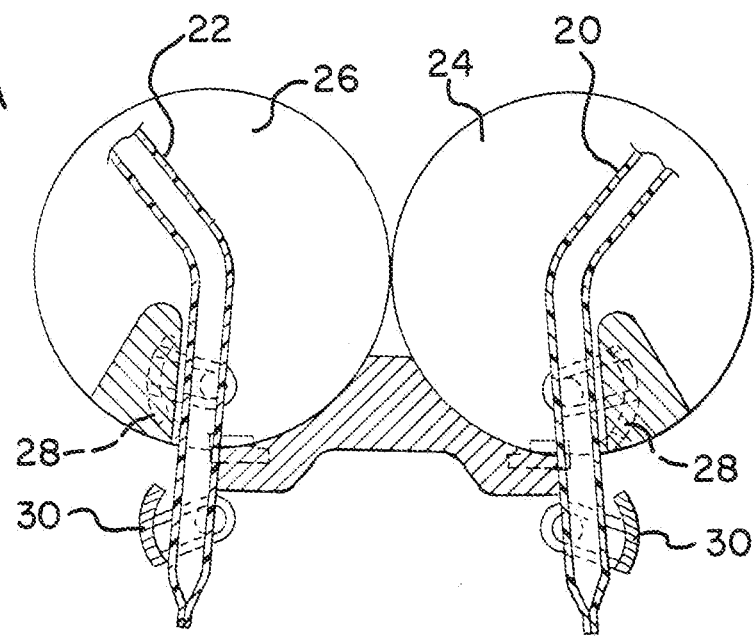
Figure 1B:
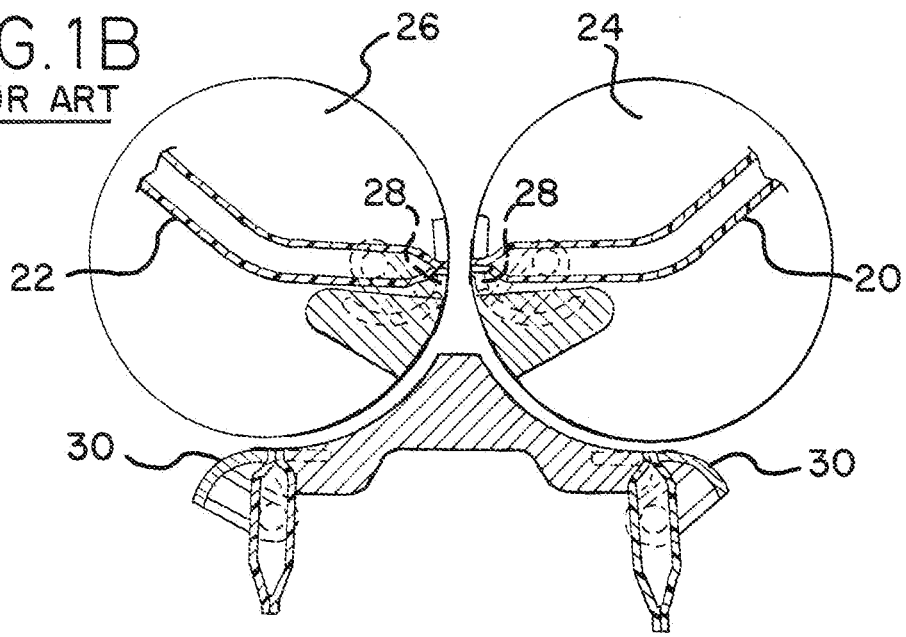

Turning now to a more detailed description, the attached drawings are provided for purposes of illustration and not limitation. As noted earlier, the present subject matter is particularly useful in opening and checking the connection site formed by heat connection devices such as illustrated in U.S. published patent application no. 2013/0153048. FIGS. 1a-1c are taken from that application and illustrate, for background and description purposes, the prior device and method for forming a heat-bonded connection between two flexible thermoplastic conduits or tubings. Without unduly elaborating on the details of such device and method, which are fully explained in the published application, sealed conduit or tubing segments 20 and 22 are each received on a rotatable disc, respectively 24 and 26. Each disc cooperates with two pair of clamping jaws 28 and 30, one of which may also be a high frequency voltage electrode for heating the clamped tubing. As seen in FIG. 1B, after the conduits or tubings are clamped and heated, the discs shift laterally to separate the clamping jaws and rotate to the positions seen in FIG. 1B. This exerts a tensile and shear force on the tubing segments, such that each tubing segment is separated from the sealed end portion of that segment. Because the clamping jaws 28 keep the ends of the segments clamped and sealed, sterility of the segments, if pre-sterilized, is maintained and, in any event, the tubing segments are safeguarded from introduction of ambient bacteria or microorganisms.

After the tubing ends are brought into a facing position, as shown in FIG. 1B, the discs move laterally again, bringing the conduit/tubing ends into direct contact. Because this happens while the tubing ends are still at elevated temperature and in semi-molten state, they form an integral, welded bond or connection site 32. Because the process results in a thermoplastic portion or "skin" 38 blocking communication between the lumen of the joined conduits or tubes, after cooling, manual manipulation is employed to break the skin and open the connection between the tubing segments for fluid flow. The present subject matter, as described below, avoids the need for manual manipulation and optionally also automates testing of the connection site integrity.

FIGS. 2-9 are diagrammatic illustrations of method and apparatus of the present subject matter for opening and/or testing the integrity of a heat-bonded connection 32 (sometimes called a heat-weld or melt-bond connection) joining two flexible, thermoplastic, conduits 20 and 22 formed by the apparatus and method such as (but not limited to) that described above and disclosed in U.S. published application no. 2013/0153048, which results in a portion of thermoplastic material that at least partially blocks flow between the conduits.

Before turning to further details of the method and apparatus, it should be noted that it is not required for the connection forming apparatus of the above published application or for the subject matter described herein that the conduits to be of the same size or material, although the material and size should be sufficiently compatible as necessary to form the heat-bonded connection. It is contemplated for application in medical fluid flow circuits that the conduits 20 and 22 will typically be flexible tubing of polyvinyl chloride ("PVC") or other flexible thermoplastic material, with an interior lumen for flowing medical fluids such as blood, blood components, anticoagulant, saline, or other liquids. As used hereinafter, "medical fluids" is intended to have a comprehensive definition to include all of the above, and "blood" is intended to include whole blood and blood components such as plasma or concentrated red cells, either with or without other blood components or added liquids such as anticoagulant. In a typical fluid flow circuit for collecting, processing or treating blood or blood components, such as the type marketed by Fenwal Inc., of Lake Zurich, Ill., the conduits may be hollow PVC tubing, a flexible thermoplastic material, having an internal lumen diameter of about 0.118-0.126 inches (3-3.2 mm) and a wall thickness of about 0.025-0.03 inches (0.635-0.762 mm). As noted above, however, this subject matter is not limited to a particular size or material for the conduits.

Turning back now to FIG. 2, the thermoplastic portion 38 blocking the connection site is also referred to as the "skin" or "web" or "portion" or "blockage." It at least partially blocks communication between lumen 34, 36 of the respective conduits 20, 22 and is exemplified by stippled area 38, which is not intended to accurately show the dimensions of the blockage, which may vary. It is anticipated that most often, the thermoplastic portion 38 formed during the connection described above will completely block communication between the lumen 34, 36, although that need not be the situation for the present method and apparatus to be useful.

Turning to FIG. 3, which depicts one embodiment of apparatus of the present subject matter and one of the first steps in the present method. The apparatus includes an occluder 40, a pressure or force sensor 42 and a pump 44. These devices may be part of a larger fluid processing device such as a blood collection and/or separation instrument, or may be part of a device devoted to making a heat-bonded connection between tubing segments of a fluid flow circuit, for example a disposable blood collection or processing flow circuit. On whatever apparatus they are used, these devices may be relatively located or disposed so that the joined conduits 20, 22 are positioned or positionable such that conduits cooperate with other respective devices disclosed herein. It may be particularly beneficial, for example, if the occuluder, sensor and pump are also located or used in association with apparatus for forming the heat bonded connection whereby the opening and/or integrity testing described can be performed soon after the heat-bonded connection is formed and while the blocking portion 38 has not fully hardened, thus potentially requiring less pressure differential to disrupt (such as break or deform) the blockage to open the connection site.

More specifically, the occluder can be any suitable device such as, for example, an external clamp (manual or automatic) that can compress the tubing closed, a stopcock or other occlusion means. Alternatively, the occluder could be an internal frangible closure member within conduit 20 of the type well known in the blood banking industry. Use of an internal frangible closure would normally require manipulation of the closure to allow flow through the conduit 20 after the opening of the blockage 38 and/or the connection integrity sensing takes place.

The pressure or force sensor 42 is located along the conduit 20 between the occluder 40 and the blockage 38 to monitor the pressure in the conduit 20 between the blockage and the occluder. This sensor may be used to detect opening of the blockage. It may also be used in combination with the opening of a blockage or, independently, to monitor the pressure over a period of time to determine connection 32 integrity and specifically to identify whether there is leakage at the connection site.

The sensor 42 may be of any suitable construction or employ any suitable technology for monitoring the internal pressure of conduit 20. This may be accomplished, for example, by monitoring the expansion of the conduit wall or the force exerted by the conduit wall on an external sensor, or other means for detecting pressure within the conduit 20.

The pump 44, which is depicted in the form a roller for purposes of illustration and not limitation, is provided on the other conduit 22, on the opposite side of the blockage 38 from the occluder 40 and pressure/force sensor 42. The pump also may be of any suitable construction or type of pump and may include, for example, a peristaltic pump employing progressive compression of the conduit 22, such as by rollers, fingers or other structures to increase the pressure within the conduit. Illustrated in FIGS. 3-6 is a single roller 46 pump arrangement for compressing the conduit 22 and increasing the internal pressure as described in more detail below.

As shown in FIGS. 3-4, after the conduits 20 and 22 are connected and the conduit 20 occluded, the pump roller 46 is pressed against conduit 22, compressing and occluding the conduit. The roller is then moved toward the connection site, where the blockage is located, as illustrated in FIG. 5, to increase the internal pressure within conduit 22 between the occluding roller and the blockage 38. Of course, this is also intended to be exemplary of any suitable pumping action and, for example, a fixed peristaltic or other type of pump may not employ the same depicted movement of roller 46 as shown in FIG. 5.

As the roller 46 approaches the connection site the internal pressure in conduit 22 between the roller and the blockage 38 (assuming it is a complete blockage of the connection site) continues to increase and the conduit 22 continues to expand. Because of the blockage, however, the sensor 42 does not sense any pressure increase within or increase in force due to expansion of the conduit 20. The internal pressure in conduit 22 increases until the blockage is broken, deformed or otherwise disrupted (see FIG. 6) to provide an open passageway between the conduits When the blockage 38 is disrupted and a flow path opened, the higher pressure within conduit 22 will now be transmitted through the connection site into conduit 20, which has remained occluded by clamp or other occluder 40. The sensor 42 will detect the pressure increase in conduit 20 via expansion of conduit 20 or by other means, and this sensing may be used to trigger an indicator to the system and/or to the user that the connection site has been opened.

Figure 7A:
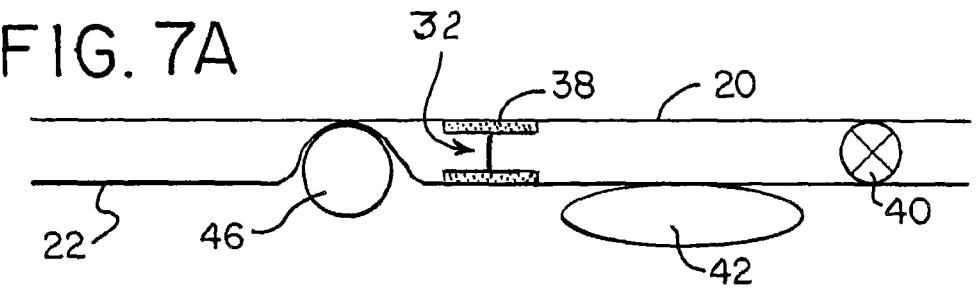
FIG. 7a is a diagrammatic sectional view like FIG. 2 and illustrating the pump roller remaining in the position of FIG. 6 for a period of time for the pressure/force sensor to sense the pressure in the respective conduit to evaluate the integrity of a connection site that, as illustrated, is intact and has no external leakage after opening.
Figure 7B:
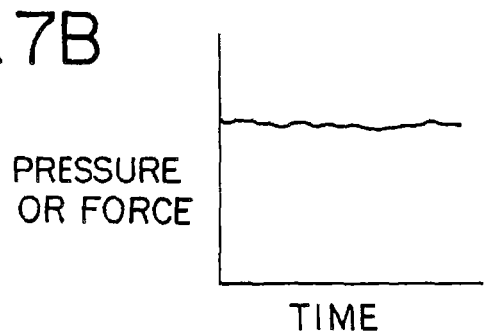
FIG. 7b is a graph of pressure or force vs. time, illustrating a pressure/force curve that would be sensed by the sensor exemplary of a connection site free of leakage.
Figure 8A:
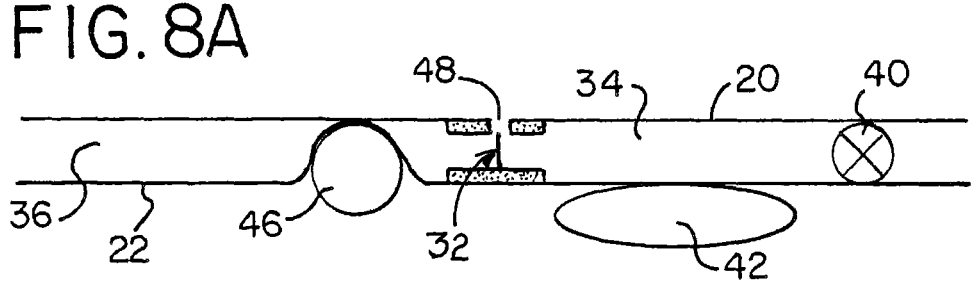
FIG. 8a is a diagrammatic sectional view like FIG. 7a and illustrating the pump roller remaining in the position of FIG. 6 for a period of time for the pressure/force sensor to sense the pressure in the respective conduit to evaluate the integrity of the connection site that, as illustrated, is not intact and has an external leak after opening.
Figure 8B:
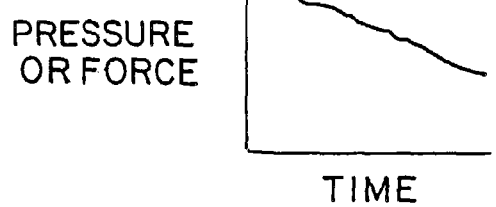
FIG. 8b is a graph of pressure or force vs. time, illustrating a pressure/force curve that would be sensed by the sensor exemplary of a connection site with an external leakage.
Figure 9:
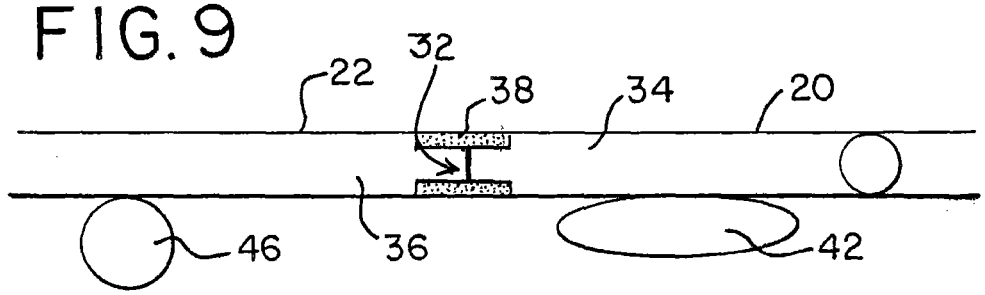
FIG. 9 is a diagrammatic sectional view of the joined conduits of FIG. 7a, after completion of integrity testing, with the pump roller no longer compressing the respective conduit and the occlusion of the conduit on the other side of the connection site having been removed.

At this point, the present system may optionally also test the connection site for leakage, such as unconnected regions at the connection site, pinholes or other apertures at the connection site. This feature can be used in combination with the above opening process or with other systems or fluid circuits or other connection forming apparatus employing a different connection technique or arrangement and not requiring the above opening process. More specifically, referring to FIGS. 7a and 7b, after the blockage has been disrupted and the connection site opened, the internal pressure is contained between the occlusion by the pump 44 in conduit 22 and the occluder 40 in conduit 20. To sense connection integrity, the sensor 42 monitors the pressure for a period of time, such as for a default period of up to about 30 seconds, such as about 20-30 seconds, to allow detection of small leaks, although it could be a longer or shorter period as described earlier. If the connection site is intact and has no leakage the sensed pressure should be substantially constant over the period of time. This is illustrated in the graph of FIG. 7b, which is a graph showing pressure sensed vs. time and depicting what is to be expected in a condition of connection integrity with no leakage. On the other hand, with reference to FIGS. 8a and 8b, if the connection site experiences leakage as diagrammatically depicted as a hole or aperture 48 in FIG. 8a, the sensed pressure will decrease over the period of time. An exemplary graph of such pressure decrease over a period of time is shown in FIG. 8b. Of course, the slope of the decrease will depend on the size of the leakage. A large leakage may cause an abrupt pressure drop whereas a small pinhole may be reflected in a much more gradual diminution in sensed pressure. By detecting the pressure over a period of time, for example up to about 30 seconds or thereabouts, the sensor is better able to detect even small leakages.

Depending on the results of the integrity testing the sensor 42 can indicate directly or via a system controller whether the connection site has passed the pressure test, demonstrating that the connection is intact, or whether it has failed, and leakage is suspected. This indication can be visual, such as indicator light, audible, such as a chime or tone, both or other. In addition, in the event leakage is detected, the sensor may even be operable on its own or through a controller, in addition to or separate from generating an alarm condition, to actually prevent continued operation of any device or system with which the sensor is associated until the user addresses the suspected leakage and clears the alarm condition.

Assuming that no suspected leak is detected, after the integrity check is completed, the roller 46 is returned to its original non-occluding position (as seen in FIG. 3) and the occlusion 40 is removed or opened, such as by releasing a clamp. The joined fluid conduits are now in condition to allow fluid flow between them, through the heat-bonded connection with better assurance that the fluid will not be contaminated due to an incomplete or non-intact connection.

FIGS. 10a and 10b shows one embodiment that serves to illustrate the use of the devices and methods described above as part of a larger fluid processing system. The system shown is for purposes of illustration and not limitation to the features of the particular system shown.

More specifically, FIG. 10a depicts a blood processing system, generally at 50, for post-collection processing blood collected from a donor. The system includes a reusable, durable processing device 52, upon which a disposable, one-time use fluid flow circuit 54 may be mounted. The illustrated durable device includes, as necessary, valves, pumps, sensors, hangers, scales, drive systems and the like for cooperating with the fluid flow circuit to control the flow of blood, blood components and other liquids through the system and carry out the desired processing. The fluid flow circuit is made up of fluid flow tubing, containers and processing devices that may be assembled onto the durable device and is, at least in part, preassembled and pre-sterilized, for conveying the blood and other associated fluids through the processing without introducing extraneous materials or contaminants. Only the disposable, one-time use fluid flow circuit contacts the blood or other liquids, thus avoiding the need to sterilize the durable hardware components and significantly reducing administrative burdens and costs associated the processing.

As illustrated, the durable portion of the system may include, among other things, flow control valves 56a-c for assisting in controlling flow through flexible plastic tubing 58 of the fluid flow circuit 54. Typically, each valve includes a pair of clamping or pinching jaws, between which fluid flow tubing of the fluid flow circuit is placed when the flow circuit is assembled onto the face of the device 52. The valves close or open the tubing in response to commands from the operating control system of the device 52 based on the particular process selected by the user. Typically the control system for device 52 employs a programmable microprocessor based controller that allows the device to be configured for one or more of different selected procedures for processing blood. In the present description, it is shown for illustrative purposes only for processing a unit of whole blood collected from a donor, for example in a prior collection procedure. The whole blood may be processed, for example, to separate it into concentrated red cells, plasma and platelets, each of which finds application in particular medical situations, thus resulting in more efficient usage of the collected blood.

The durable device 52 may also include pumps 60a-c, such as peristaltic type pump, operable on the tubing 58 of the fluid flow circuit to direct flow therethrough, a station 62 for receiving and interacting with a blood separation device, and various other sensors, weigh scales and other components to control fluid processing through the fluid flow circuit.

In relation to the present subject matter, the durable device may include heat-bonding connection site, generally at 64, that may include apparatus such as but not limited to that described in U.S. publish application no. 2013/0153048, for forming a heat-bonded connection, such as a sterile connection, between tubing (conduit) portions of the fluid circuit. In the illustrated embodiment, the connection formed is between a flexible thermoplastic (PVC) tubing segment 66 of the preassembled disposable fluid circuit 54 and flexible thermoplastic (PVC) flow tubing segment 68 attached to a container or bag 70 of collected blood.

The heat bonding connection device site 64 is diagrammatically shown in FIG. 10b, except for the actual connection forming apparatus, specifically FIG. 10b depicts the two tubing segments 66 and 68 at the site prior to formation of the heat bonded connection. This site 64 of the device also may include a pressure/force sensor 72 for sensing pressure in the blood bag tubing segment 68, as will be described more fully later.

Turning now to the disposable fluid flow circuit 54 in the illustrated in FIG. 10a example, the preassembled circuit includes a blood separation device 74, containers or bags 76 (e.g., containing RBC additive solution), 78 (e.g., for receiving concentrated RBCs) and 80 (e.g., for receiving plasma), leukoreduction filter 82 and associated flexible tubing 58 connecting the various components in a fluid flow relationship. The preassembled circuit may be pre-sterilized, and the tubing extension or segment 66 to be joined to the blood bag may terminate at a heat sealed end to preserve sterility.

When mounted on the separation device, the components of the preassembled flow circuit are placed on or in their selected locations, the blood separation device 74 in the station 62, the tubing in the valves 56, sensors, and pumps 60 and the bags 76-80 on the various hangers.

To carry out the illustrated blood processing, the bag of collected blood 70 is suspended from the appropriate hook or hanger and tubing segment 68 is placed in valve 56*a*, and in association with the pressure/force sensor 72. Together with tubing segment 66 of the preassembled fluid circuit, tubing segment 68 are placed in operative position on the connection forming apparatus. This is the position shown diagrammatically in FIG. 10*b*.

Figure 11:
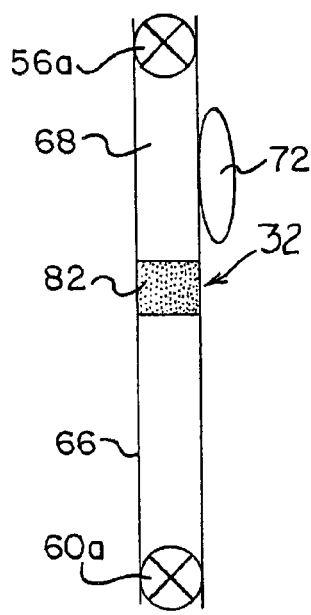
FIGS. 11-13 are diagrammatic views of the portion shown in FIG. 10b, illustrating opening of the connection site in a fluid circuit, similar to FIGS. 4-6.
Figure 12:
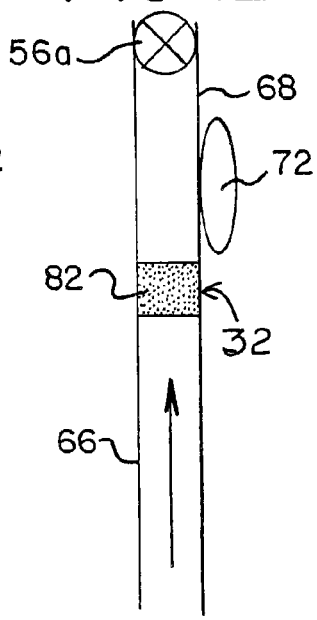

Referring to FIGS. 11-12, FIG. 11 diagrammatically shows the tubing segments 66, 68 after the connection is formed by the connection apparatus, and a thermoplastic portion or skin 82 is formed during the connection process and blocks flow through the tubing segments. In a manner similar to that described earlier, the pump 60*a* occludes the fluid circuit tubing 58, which extends from tubing segment 66, and valve 56*a* clamps the tubing segment 68 closed. Valve 56*b* is upstream of the junction between tubing segment 66 and the remainder of the fluid flow circuit and also closes the tubing at that location.

Figure 13:
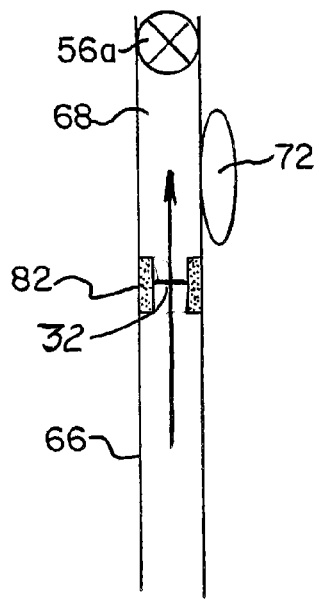
Figure 14A:
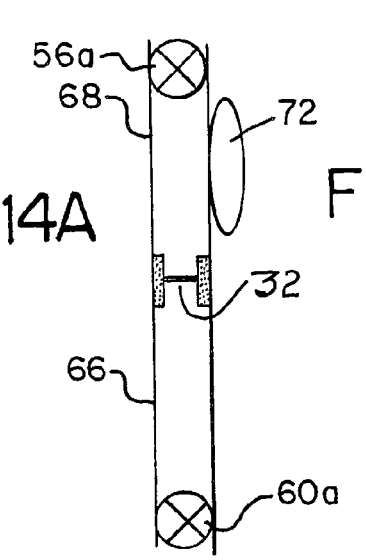
FIGS. 14a and 14b are diagrammatic views of the portion shown in FIG. 10b, illustrating an integrity check of a connection site that is free of external leakage and the typical pressure/force vs. time graph that would reflect such connection site to the sensor.

Within a relatively short time after the heat-bonded connection is formed, the pump 60*a* is activated and increases the pressure in the tubing segment 66 as seen in FIG. 11, until the thermoplastic blocking portion 82 is disrupted and opened to flow, as illustrated in FIG. 13.

Figure 14B:
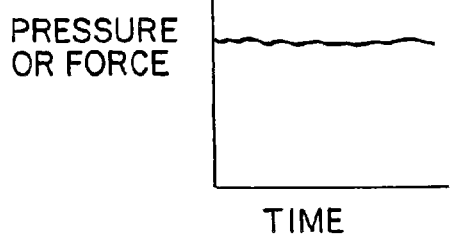

Optionally, the pressure/force sensor 72 monitors the pressure in the tubing segment 68 to evaluate the integrity of the connection, as described earlier. If the connection between the tubing segments 66, 68 is intact and without leaks, the pressure/force vs time relationship sensed by the sensor will be substantially as shown in FIG. 14*b*, and the device control system may so indicate to the user, who may proceed with the blood processing. If, on the other hand, the connection site is not intact and experiencing leakage, the pressure/force vs time relationship will be similar to that shown in FIG. 15*b*, and the device control system may generate an audio or visual alarm to the user and/or may prevent continuation of the process until the user intervenes.

In conclusion, although the present subject matter has been described with reference to specific devices and methods, that is for the purpose of description and not limitation. It is contemplated, for example, that this subject matter may be used with other devices, systems and methods, and reference should be made to the attached claims for an understanding of the scope of certain aspects of the present subject matter.

The invention claimed is:

1. A method for opening a heat-bonded connection formed between two hollow, flexible, thermoplastic conduits, which connection includes a frangible portion of thermoplastic material formed during the heat bonding and at least partially blocking internal communication between the conduits, the method including: creating a pressure difference between the inside of at least one of the conduits and the ambient atmosphere sufficient to cause expansion of a wall of the tubing conduit in the vicinity of the frangible portion of thermoplastic material to disrupt the frangible portion and reduce the blocking.

2. The method of claim 1 in which the pressure difference is created before the thermoplastic material at the connection has fully hardened from the heat-bonded connection.

3. The method of claim 1 in which the pressure difference is created when the thermoplastic material has a temperature above its glass transition temperature.

4. The method of claim 1 in which the pressure difference is created within about 10 seconds of the formation of the heat-bond connection.

5. The method of claim 1 in which the pressure difference is created by increasing pressure inside of the tubular conduit above ambient pressure.

6. The method of claim 1 including occluding one of the thermoplastic conduits and increasing the pressure in the other of the thermoplastic conduits until the frangible portion is disrupted.

7. The method of claim 6 including sensing the pressure in one of the conduits after the frangible portion is disrupted to determine the integrity of the heat-bond.

8. The method of claim 7 including sensing the pressure over a time period.

9. The method of claim 7 in which the pressure is sensed from an initiation of the step of increasing pressure in the other of the conduits.

10. The method of claim 6 including sensing the pressure in the one of the conduits to determine disruption of the frangible portion.

11. The method of claim 6 including increasing the pressure in the other of the conduits until a pressure increase is sensed in the one of the conduits.

12. The method of claim 11 in which the pressure increase does not exceed a burst pressure of the other conduit.

13. A method of forming and opening a heat bonded connection between two thermoplastic tubes comprising:
  heating one end of each tube until it is in semi-molten state and bringing the ends into direct contact to form a heat bonded connection therebetween which includes a frangible portion of the thermoplastic tube material at partially blocking internal fluid flow communication between the tubes;
  increasing pressure within one of the tubes when the thermoplastic material at the connection site is above the glass transitional temperature of such thermoplastic material while occluding the other of the tubes at an occlusion location;
  sensing the pressure in the other of the tubes between the connection site and occlusion location while the pressure is increased in the one tube;
  increasing the pressure within the one tube until a pressure increase is sensed in the other tube indicative of disruption of the frangible portion;
  continuing to sense the pressure in the other tube for a period of time after the disruption to determine the integrity of the heat bonded connection; and
  generating an audible or visual alarm in the event the continued sensing of pressure in the other tube indicates leakage at the connection site.

14. The method of claim 13 including sensing the pressure in the other tube for up to about 30 seconds after disruption.

15. The method of claim 13 wherein the pressure is increased in the one tube within less than about 10 seconds after the connection is formed.

16. The method of claim 13 wherein the pressure in the one tube is increased to about 19-29 psi.

17. The method of claim 13 wherein the tubes are made of polyvinylchloride.

18. The method of claim 17 wherein the tubes have an internal lumen diameter of about 0.118-0.126 inches (3.0 mm -3.2 mm) and a wall thickness of about 0.025-0.03 inches (0.63 mm -0.76 mm).

19. The method of claim 18 wherein the pressure is increased in the one tube within less than about 10 seconds after connection is formed and the pressure in the other tube is sensed for a time period of up to about 30 seconds after disruption; and the occlusion opened if no leak is detected within the time period.

\* \* \* \* \*